United States Patent [19]

Su et al.

[11] Patent Number: 4,889,693
[45] Date of Patent: Dec. 26, 1989

[54] APPARATUS FOR VENTING OF GASES FROM CONTACT LENS CASES

[75] Inventors: Kai C. Su, Alpharetta; Jack C. White, Stone Mountain, both of Ga.

[73] Assignee: Ciba-Geigy Corporation, Ardsley, N.Y.

[21] Appl. No.: 146,954

[22] Filed: Jan. 22, 1988

[51] Int. Cl.$^4$ .............................................. A61L 2/18
[52] U.S. Cl. .................................... 422/113; 422/300; 422/301; 422/310; 206/5.1; 206/438; 220/209; 220/303; 220/367; 220/368
[58] Field of Search ............... 422/113, 297, 299, 300, 422/310, 301; 206/5.1, 438; 220/209, 303, 367, 368, 366

[56] References Cited

U.S. PATENT DOCUMENTS

| | | | |
|---|---|---|---|
| 4,011,941 | 3/1977 | Parsons | 206/5.1 |
| 4,396,583 | 8/1983 | LeBoeuf | 422/301 |
| 4,457,327 | 7/1984 | Pepper | 422/310 X |
| 4,637,919 | 1/1987 | Ryder et al. | 422/300 |
| 4,750,610 | 6/1988 | Ryder | 422/300 X |

Primary Examiner—Barry S. Richman
Assistant Examiner—Lynn M. Kummert
Attorney, Agent, or Firm—Irving M. Fishman

[57] ABSTRACT

An appliance for disinfecting/sterilizing contact lenses having a valve for the venting of gases liberated from the lens solution in the form of a deformable, polymeric plug which is movable between a closed and an open position, depending on the pressure of the gases.

2 Claims, 1 Drawing Sheet

APPARATUS FOR VENTING OF GASES FROM CONTACT LENS CASES

BACKGROUND OF THE INVENTION

This invention relates to an improved container for the chemical sterilizing or disinfecting of soft contact lenses and, more particularly, to a device for the venting from contact lens holding appliances of gases liberated by contact lens solutions.

Hydrophilic contact lenses are commonly cleaned or sterilized in a bactericide solution, such as a 3% solution of hydrogen peroxide along with a hydrogen peroxide decomposition catalyst, for several hours. By means of the catalyst, the hydrogen peroxide is rapidly decomposed into water and oxygen. If the container holding the solution is completely sealed, the liberated gas may create undue pressure causing the container or case to fracture, thereby destroying its integrity. Therefore, it is necessary to vent the liberated oxygen from whatever appliance contains the solution and lenses.

A prior art venting method was simply to allow the oxygen to escape through an opening in the top of the case, but the liquid could also spill out if the case was tilted or turned over. Such loss of solution would likely cause the lens to dehydrate. Also, any solution which passed through the opening could damage the clothing of the user.

U.S. Pat. No. 4,396,583 to LaBoeuf and U.S. Pat. No. 4,637,919 to Ryder et al. disclose vented lens disinfecting appliances which employ a hydrophobic membrane filter disposed across the vent that is impermeable to the solution but is permeable to the liberated oxygen gas. The disadvantages of that filter include the clogging of the membrane pores during repeated uses of the appliance due to dehydrate solution ingredients and various materials released into solution from the lens surfaces. Over time, the gases liberated from the disinfecting solution cannot be satisfactorily vented, possibly fracturing the case.

SUMMARY OF THE INVENTION

The disadvantages of the prior art are overcome by the present invention which is a valve means that replaces the above-mentioned membrane, the valve being in the form of a deformable, polymeric plug that is positioned within the passageway formed between the interior of the container and the atmosphere. In its normal or closed position, the plug does not allow the solution to pass therethrough. However, as a result of the pressure of the gases released from the lens solution reaching a certain level, the plug moves to an open position that allows the gases to vent to the atmosphere.

DETAILED DESCRIPTION OF THE EMBODIMENTS

A. First Embodiment

Figure 1:
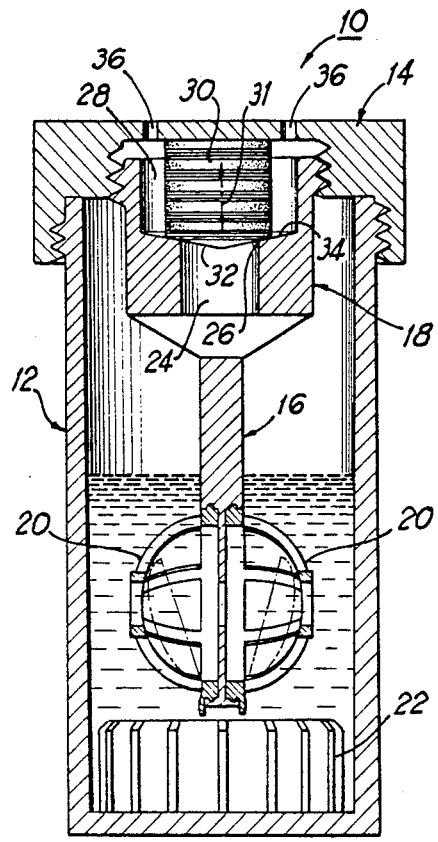
FIGS. 1-3 are vertical cross-sectional views through various lens cases showing three embodiments of the venting means of the present invention.

Referring to FIG. 1, the numeral 10 denotes generally an example of a commercially available contact lens disinfectant/sterilizing appliance comprising a cylindrical container 12 having a removable screw cap 14 threaded onto its upper open end. An elongated frame 16 depends from the bottom of circular member 18 secured to the underside of cap 14 into the interior of the container 12. Left and right eye lens holding means 20 are mounted at the bottom of the frame 16 above the catalyst member 22.

The member 18 includes a first cavity 24 longitudinally extending therethrough which is in flow communication through its lower end with the interior of the container 12 and, at the upper end of cavity 24, with the bottom of a second cavity 28 through opening 26. The diameter of the second cavity 28 is greater than that of the first cavity 24.

A deformable, polymeric, cylindrically shaped plug 30 is disposed within cavity 28. The plug 30 has a diameter which is greater than cavity 24 but is less than cavity 28 and is of a length such that, in its normal closed position as shown in FIG. 1, the bottom 32 of the plug 30 rests on the shelf 34 formed at the bottom of the second cavity 28, sealing the opening 26 at the juncture of the two cavities. A plurality of vertical openings 36 through cap 14 connect the interior of the second cavity 28 with the atmosphere. The cavities 24, 28 and openings 26, 36 form a venting passageway leading from the interior of the container 12 to the exterior of the appliance 10.

In operation, the hydrogen peroxide solution and the catalyst member 22 are placed into the container 12 and cap 14 is secured thereonto. The contact lenses within the holding means 20 are then immersed in the solution from which oxygen begins to be liberated as a result of the decomposition of the hydrogen peroxide.

After a certain amount of oxygen enters the first cavity 24, the pressure therein increases to a predetermined level. The plug 30 is then deformed along its longitudinal axis 31 to assume its open position (not shown), whereby the bottom of the plug 30 rises from its sealing engagement with shelf 34. The oxygen gas can then pass from the first cavity 24 through opening 26 into the second cavity 28 to be vented into the atmosphere through openings 36.

The plug 30 is maintained in its open position until a sufficient amount of oxygen has been released from the solution. At that time, the pressure against the bottom of the plug 30 drops below the predetermined level, and the plug 30 assumes its closed position which thereby prevents any additional gas to be vented from the container 12 and also prevents any of the solution from spilling out.

The above-mentioned predetermined pressure level is set at well below the failure level of the appliance 10. The criteria of geometry and the composition of the plug 30 assure that the plug 30 is operative at that level. Thus, it can be seen that the plug 30 of the present invention can continually perform its venting function without ever becoming clogged as with the prior art membranes.

B. Second Embodiment

Figure 2:
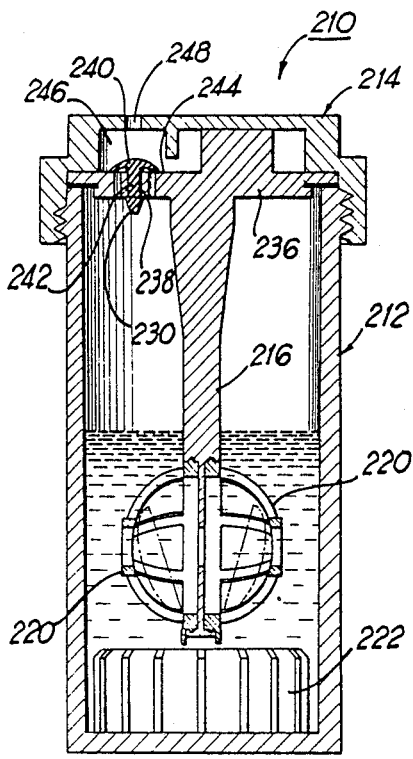

The second embodiment of the present invention is shown in FIG. 2 and includes another commercially available lens disinfectant appliance 210 comprising container 212, cap 214, frame 216, lens holding means 220 and catalyst member 222.

Frame 216 is attached to the underside of support member 236 that is mounted within cap 214. A vertical bore 238 extends through support member 236 and communicates the interior of container 212 with vent opening 248 through the cap 214.

Disposed through bore 238 is a mushroom-shaped deformable, polymeric plug 230 having a head portion 240 and a depending body section 242 which resides within bore 238. The bottom of head portion 240 normally rests on surface 244 of inner chamber 246 formed by support member 236 and cap 214. The diameter of body section 242 is such that it snugly fits within bore 238. A plurality of channels are disposed in vertical, spaced alignment about the exterior surface of body section 242. The bore 238, inner chamber 246 and opening 248 form a vent passageway from the interior of the container 212 to the atmosphere.

The operation of the appliance 210 is the same as for the first embodiment. When the predetermined level of oxygen pressure is reached within the interior of container 212, the gas within the channels on body section 242 unseats the head portion 240 from its sealing engagement with surface 244 and causes the plug 230 to assume its open position (not shown), allowing the oxygen to exit the container 212 into the atmosphere through opening 248. After the pressure of the liberated oxygen drops below a predetermined level, the head portion 240 assumes its closed position, as shown in FIG. 2.

C. Third Embodiment

Figure 3:
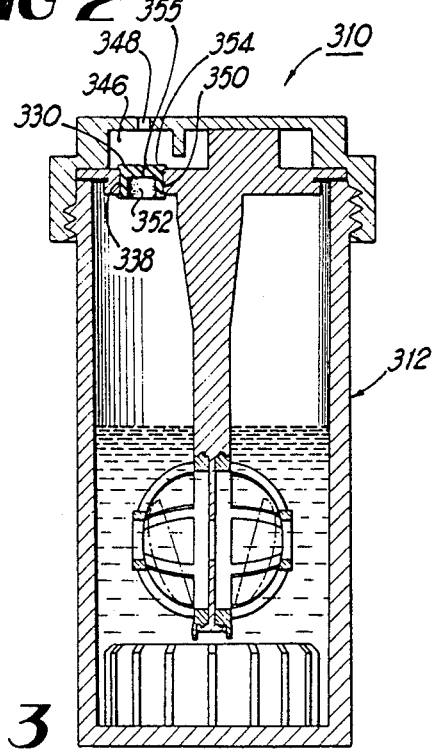

In the third embodiment, shown in FIG. 3, the container 312 and its associated elements, are identical in construction to container 212, with the only difference being the shape of the deformable plug 330 within bore 338. The plug 330 is of a deformable polymeric composition and has a round body portion 350 and an open bottom that define a chamber 352 and a top 354. A slit 355 is formed through the top 354.

The slit 355 is normally closed, not allowing any liquids or gases to pass therethrough. However, when the pressure of the gases released from the contact lens solution reaches a certain point, the gas within chamber 352 forces the slit 355 open, allowing the gas to pass therethrough into inner chamber 346 and out opening 348. After a sufficient amount of the gas has been liberated from solution, the pressure against the slit 355 decreases, allowing the slit 355 to close.

It is understood, of course, that the plugs 30, 230 and 330 are only illustrative embodiments and that the present invention can be used in lens solution containers of any construction. Any element which can function, in essence, as a check-valve for the venting of gases above a certain pressure and that can be utilized in a convention contact lens disinfecting/sterilizing container can be utilized.

WHAT WE CLAIM IS:

1. An improvement in an appliance for disinfecting/sterilizing contact lenses of the type having a container with an open end, means for holding the lenses within an interior of said container, a cap that detachably closes said open end and having means defining an opening therethrough, and a passageway in said container which provides communication between the interior of said container and the atmosphere through said opening to provide a vent for gases liberated from disinfecting/sterilizing solution therein, the improvement comprising: said passageway being substantially vertically extending, a rigid supporting member extending across said passageway through said container and said container interior and defining therethrough a bore communicating with said passageway and with said interior, a valve means disposed within said passageway, said valve means being selectively movable between a normal, closed position which seals said passageway and an open position which allows gases to exit said container through said passageway and through said opening in said cap, said valve means comprising a deformable plug being positioned within said bore and comprising a circular body having an open bottom portion which defines a chamber and a top on said body, said top having a slit therethrough which is movable into said open position by gas being liberated from solution in said container.

2. An improvement in an appliance for disinfecting/sterilizing contact lenses of the type having a container with an open end, means for holding the lenses within an interior of said container, a cap that detachably closes said open end and having means defining an opening therethrough, and a passageway in said container which provides communication between the interior of said container and the atmosphere through said opening to provide a vent for gases liberated from disinfecting/sterilizing solution therein, the improvement comprising:

said passageway being substantially vertically extending through said container interior and comprising a first cavity having a bottom which is open to said interior of said container and an open top, a second cavity including a bottom which is in flow communication with said top of said cavity so as to define a bore, said second cavity being larger in dimension than said first cavity and wherein said opening in said cap is in flow communication with said second cavity, and a deformable plug being located within said second cavity and having a round body portion, a bottom surface on said body portion which normally overlies said bore and a top surface on said body portion which engages an underside of said cap, said plug being selectively movable along the longitudinal axis of said body portion between a normal, closed position which seals said bore and an open position which allows gases to exit said container through said first cavity, then through said bore, then through said second cavity and then through said opening in said cap.

* * * * *